US006576615B2

(12) United States Patent
Phan et al.

(10) Patent No.: US 6,576,615 B2
(45) Date of Patent: Jun. 10, 2003

(54) 4'-O-SUBSTITUTED TYLOSIN ANALOGS

(75) Inventors: Ly Tam Phan, Malden, MA (US); Tianying Jian, Boston, MA (US); Yao-Ling Qiu, Somerville, MA (US); Yat Sun Or, Cambridge, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/007,744

(22) Filed: Nov. 8, 2001

(65) Prior Publication Data

US 2003/0092639 A1 May 15, 2003

(51) Int. Cl.[7] ........................ A61K 31/70; C07H 17/08; C07H 1/00

(52) U.S. Cl. .......................... 514/30; 536/7.1; 536/18.5

(58) Field of Search ................................ 536/7.1, 18.5; 514/30

(56) References Cited

U.S. PATENT DOCUMENTS

| | | | | |
|---|---|---|---|---|
| 4,652,638 A | | 3/1987 | Fujiwara et al. | 536/7.1 |
| 4,820,694 A | | 4/1989 | Debono et al. | 514/30 |
| 5,032,581 A | * | 7/1991 | Lukacs et al. | 514/30 |
| 5,444,174 A | * | 8/1995 | Ajito et al. | 536/7.1 |

FOREIGN PATENT DOCUMENTS

| | | |
|---|---|---|
| EP | 0262903 A2 | 4/1988 |
| EP | 0262905 A2 | 4/1988 |

* cited by examiner

*Primary Examiner*—Elli Peselev
(74) *Attorney, Agent, or Firm*—Gaetano D. Maccarone, Esq.

(57) ABSTRACT

There are described novel 4' substituted tylosin analogs and pharmaceutically acceptable compositions comprising a therapeutically effective amount of a compound of the invention in combination with a pharmaceutically acceptable carrier. Also described is a method for treating bacterial infections by administering to a mammal a pharmaceutical composition containing a therapeutically-effective amount of a compound of the invention, and processes for the preparation of such compounds.

14 Claims, No Drawings

4'-O-SUBSTITUTED TYLOSIN ANALOGS

TECHNICAL FIELD

The present invention relates to novel macrolides having antibacterial activity and useful in the treatment and prevention of bacterial infections. More particularly, the invention relates to a novel class of 4'-substituted 16-membered macrolides, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) exhibits a wide range of characteristics (antibacterial spectrum, side-effects and bioavailability). Among the commonly used macrolides are erythromycin and josamycin.

The 16-membered ring macrolide antibiotics constitute an important clinically useful series of naturally occurring compounds within the macrolide class of antibiotics, as they show some advantages over 14-membered ring compounds (gastrointestinal tolerance and activity against strains expressing resistance of the inducible type). Sixteen membered macrolides usually contain an amino disaccharide -4-O-(L-mycarosyl)-D-mycaminose and/or D-desosamine. One class has only neutral sugars. The sixteen membered macrolides can be classified into two major groups—the leucomycins and the tylosin series. The tylosin series is divided into two groups-IIA and IIB which differ at the C-6-side chain and the nature of the sugars on the chromophore. Tylosin consists of a substituted 16-membered ring lactone (tylonolide), an aminosugar (D-mycaminose) attached to C-5, two neutral sugars (D-mycinose attached at C-23 and L-mycarose attached at C-4') and an acetaldehyde at C-6.

Considerable research efforts have been carried out on tylosin and its derivatives but not much success has been observed with this subclass. The search for macrolides active against MLS-resistant strains (MLS=Macrolides-Lincosamides-Streptogramines) has become a major goal, in addition to improving the overall profile of the macrolides in terms of acid stability, tolerance and pharmacokinetics.

SUMMARY OF THE INVENTION

The present invention provides a novel class of 4'-substituted tylosin analogs possessing increased antibacterial activity toward Gram positive and Gram negative bacteria as well as macrolide resistant Gram positives. In addition, the present invention provides a class of 4'-substituted tylosin derivatives that are more acid stable and overcome bacterial resistance.

In one embodiment, the present invention provides compounds represented by Formula I, or a pharmaceutically acceptable salt, ester or prodrug thereof:

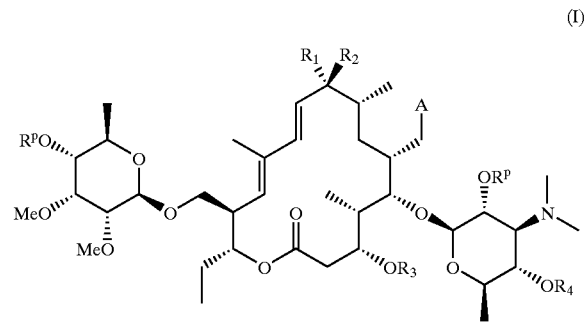

(I)

In Formula I,
A is selected from the group consisting of:
(1) —CHO or a protected aldehyde;
(2) —CH$_2$X, wherein X is selected from the group consisting of:
  a. hydroxy or protected hydroxy; and
  b. halogen;
(3) —CN;
(4) —CH=N—NR7R8, wherein R7 and R8 are each independently selected from hydrogen, C1–C6-alkyl, optionally substituted with one or more substituents selected from the group consisting of

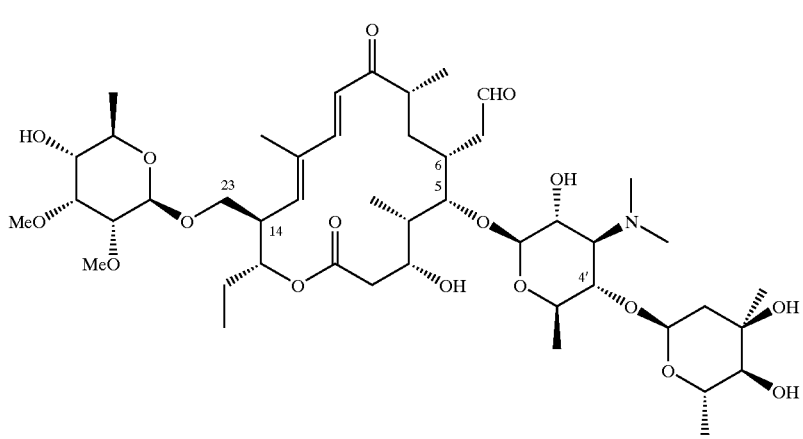

Tylosin halogen, aryl, substituted aryl, heterocyclic and substituted heterocyclic, C2–C6-alkenyl, optionally substituted with one or more substituents selected from the group consisting of halogen, aryl, substituted aryl, heterocyclic and substituted heterocyclic, C2–C6-alkynyl, optionally substituted with one or more substituents selected from the group consisting of halogen, aryl, substituted aryl, heterocyclic and substituted heterocyclic or R7R8 taken with the nitrogen atom to which they are connected form a 3- to 7-membered ring which may optionally contain a hetero function selected from the group consisting of —O—, —NH—, —N(C1–C6-alkyl)-, —N(aryl)-, —N(heteroaryl)- , —S—, —S(O)— and —S(O)$_2$—;
  (5) —CH=N—OR7, wherein R7 is as previously defined;
  (6) substituted or unsubstituted imidazole, arylimidazole or heteroarylimidazole;
  (7) substituted or unsubstituted oxazole, aryloxazole or heteroaryloxazole, substituted or unsubstituted thioxazole, arylthioxazole or heteroarylthioxazole;
  (8) substituted or unsubstituted imidazoline, arylimidazoline or heteroarylimidazoline;
  (9) substituted or unsubstituted oxazoline, aryloxazoline or heteroaryloxazoline; and
  (10) substituted or unsubstituted thioxazoline, arylthioxazoline and heteroarylthioxazoline;
R1 and R2 are each independently selected from the group consisting of:
  (1) hydrogen;
  (2) hydroxy;
  (3) protected hydroxy;
  (4) —OC(O)—C1–C12-alkyl, optionally substituted with one or more substituents selected from the group consisting of halogen, aryl, substituted aryl, heterocyclic, substituted heterocyclic, O—R7 and NR7R8 where R7 and R8 are as previously defined;
  (5) —O—R7, where R7 is as previously defined;
  (6) halogen;
  (7) —NR7R8, where R7 and R8 are as previously defined; and
  (8) R1 and R2 taken together are oxo;
R3 is selected from the group consisting of:
  (1) hydrogen;
  (2) a hydroxy protecting group;
  (3) —C(O)—C1–C12-alkyl, optionally substituted with one or more substituents selected from the group consisting of halogen, aryl, substituted aryl, heterocyclic, substituted heterocyclic, O—R7 and NR7R8 where R7 and R8 are as previously defined;
  (4) C1–C6-alkyl, optionally substituted with one or more substituents selected from the group consisting of halogen, aryl, substituted aryl, heterocyclic, substituted heterocyclic, O—R7 and NR7R8 where R7 and R8 are as previously defined;
  (5) C2–C6-alkenyl, optionally substituted with one or more substituents selected from the group consisting of halogen, aryl, substituted aryl, heterocyclic, substituted heterocyclic, O—R7 and NR7R8 where R7 and R8 are as previously defined; and
  (6) C2–C6-alkynyl, optionally substituted with one or more substitutents selected fron the group consisting of halogen, aryl, substituted aryl, heterocyclic, substituted heterocyclic, O—R7 and NR7R8 where R7 and R8 are as previously defined;
R4 is —M—Y,
  where M is:
    (1) absent,
    (2) —C(O)—,
    (3) —C(O)N(R7)-, where R7 is as previously defined,
    (4) —C1–C6-alkyl-N(R7)-, where R7 is as previously defined,
    (5) —C2–C6-alkenyl-N(R7)-, where R7 is as previously defined, or
    (6) —C2–C6-alkynyl-N(R7)-, where R7 is as previously defined;
  and where Y is:
    (1) hydrogen,
    (2) hydroxy protecting group,
    (3) C1–C6-alkyl, optionally substituted with one or more substituents selected from the group consisting of halogen, aryl, substituted aryl, heterocyclic and substituted heterocyclic, —OR7 where R7 is as previously defined,
    (4) C2–C6-alkenyl, optionally substituted with one or more substituents selected from the group consisting of halogen, aryl, substituted aryl, heterocyclic and substituted hetreocyclic, —OR7 where R7 is as previously defined,
    (5) C2–C6-alkynyl, optionally substituted with one or more substituents selected from the group consisting of halogen, aryl, substituted aryl, heterocyclic and substituted heterocyclic, —OR7 where R7 is as previously defined,
    (6) aryl,
    (7) substituted aryl,
    (8) heterocyclic, or
    (9) substituted heterocyclic; and
$R^P$ is hydrogen or a hydroxy protecting group.

In another embodiment, the present invention provides a process for preparing novel compounds represented by Formula I wherein the groups A, R1, R2, R3, R4 and $R^P$ are as previously defined.

DETAILED DESCRIPTION OF THE INVENTION

A first embodiment of the invention is a compound represented by Formula I as described above.

Representative compounds of the invention are those selected from the group consisting of:
  Compound of Formula I: A=—CHO, R1 and R2 taken together=O, R3=H, R4=—CH$_2$CHCH$_2$ and $R^P$=H;
  Compound of Formula I: A=—CHO, R1 and R2 taken together=O, R3=—CH$_2$CHCH$_2$, R4=H and $R^P$=H;
  Compound of Formula I: A=—CHO, R1 and R2 taken together=O, R3=H, R4=—CHCHCH$_2$-(3-quinolyl) and $R^P$=H;
  Compound of Formula I: A=—CHO, R1 and R2 taken together=O, R3=H, R4=—CH$_2$CHCH-(3-quinolyl), and $R^P$=H;
  Compound of Formula I: A=—CHO, R1 and R2 taken together=O, R3=—CH$_2$CHCH-phenyl, R4=H and $R^P$=H;
  Compound of Formula I: A=—CHO, R1 and R2 taken together=O, R3=—CHCHCH$_2$-(3-quinolyl), R4=H and $R^P$=H; and
  Compound of Formula I: A=—CHO, R1 and R2 taken together=O, R3=—CH$_2$CHCH-(3-quinolyl), R4=H and $R^P$=H.

Definitions

The terms "$C_1$–$C_3$-alkyl," "$C_1$–$C_6$-alkyl" or "C1–C12-alkyl," as used herein, refer to saturated, straight- or branched-chain hydrocarbon radicals containing between one and three, one and six or one and twelve carbon atoms, respectively. Examples of $C_1$–$C_3$ alkyl radicals include, but are not limited to, methyl, ethyl, propyl and isopropyl, and examples of $C_1$–$C_6$-alkyl radicals include, but are not limited to, methyl, ethyl, propyl, isopropyl, n-butyl, tert-butyl, neopentyl and n-hexyl, and examples of C1–C12-alkyl radicals include, but are not limited to, methyl, ethyl, propyl, isopropyl, n-butyl, tert-butyl, neopentyl, n-hexyl, n-octyl, n-decyl, and n-dodecyl.

The term "C2–C6-alkenyl," as used herein, refers to straight- or branched-chain hydrocarbon radicals containing between two and six carbon atoms with one or more double bonds in the chain. Examples of C2–C6-alkenyl include, but are not limited to, propenyl, isobutenyl, 1,3-hexadienyl, n-hexenyl, and 3-pentenyl.

The term "C2–C6-alkynyl," as used herein, refers to straight- or branched-chain hydrocarbon radicals containing between two and six carbon atoms with one or more triple bonds in the chain optionally containing one or more double bond. Examples of C2–C6-alkynyl include, but are not limited to, propynyl, isopentynyl, 1,3-hexadiynyl, n-hexynyl, 3-pentynyl, and 1-hexen-3-ynyl.

The term "$C_1$–$C_6$-alkoxy," as used herein, refers to a $C_1$–$C_6$-alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The term "$C_1$–$C_3$-alkyl-amino," as used herein, refers to one or two $C_1$–$C_3$-alkyl groups, as previously defined, attached to the parent molecular moiety through a nitrogen atom. Examples of $C_1$–$C_3$-alkyl-amino include, but are not limited to, methylamino, dimethylamino, ethylamino, diethylamino, and propylamino.

The term "aprotic solvent," as used herein, refers to a solvent that is relatively inert to proton activity, i.e., not acting as a proton-donor. Examples include, but are not limited to, hydrocarbons, such as for example, hexane and toluene, and the like, halogenated hydrocarbons, such as, for example, methylene chloride, ethylene chloride, chloroform, and the like, heterocyclic compounds, such as, for example, tetrahydrofuran, N-methyl pyrrolidinone, and the like and ethers such as for example, diethyl ether, bis-methoxymethyl ether and the like. Such compounds are well known to those skilled in the art, and it will be apparent to those skilled in the art that individual solvents or mixtures thereof may be preferred for specific compounds and reaction conditions, for example, depending upon such factors as the solubility of reagents, reactivity of reagents and preferred temperature ranges. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the Techniques of Chemistry Series, John Wiley & Sons, NY, 1986.

The term "aryl," as used herein, refers to unsubstituted carbocyclic aromatic groups including, but not limited to, phenyl, 1- or 2-naphthyl and the like.

The terms "$C_3$–$C_5$-cycloalkyl- and $C_3$–$C_7$-cycloalkyl," as used herein refer to carbocyclic groups of 3 to 5 or 3 to 7 carbon atoms, respectively, such as for example, cyclopropyl, cyclobutyl, cyclopentyl, cyclohexyl, and cycloheptyl.

The term "$C_1$–$C_3$-alkyl-$C_3$–$C_5$-cycloalkyl," as used herein refers to a $C_3$–$C_5$-cycloalkyl radical, as defined above, attached to a $C_1$–$C_3$-alkyl radical by replacement of a hydrogen atom on the latter.

The terms "halo" and "halogen," as used herein, refer to an atom selected from fluorine, chlorine, bromine and iodine.

The term "heteroaryl," as used herein, refers to a cyclic aromatic radical having from five to ten ring atoms of which one ring atom is selected from S, O and N; zero, one or more ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl," as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heterocyclic," as used herein, refers to heterocycloalkyl and heteroaryl. The term "substituted heterocyclic," as used herein, refers to substituted heterocycloalkyl and substituted heteroaryl.

The term "substituted aryl," as used herein refers to an aryl group, as defined herein, substituted by independent replacement of one or more of the hydrogen atoms therein with, for example, but not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_7$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, substituted aryl, heteroaryl, substituted heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heteroaryl," as used herein refers to a heteroaryl group as defined herein substituted by independent replacement of one or more of the hydrogen atoms therein with, for example, but not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heterocycloalkyl," as used herein, refers to a heterocycloalkyl group, as defined above, substituted by independent replacement of one or more of the hydrogen atoms therein with, for example, but not limited to, F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$-$C_6$-alkyl, NHCONH-aryl, NHCONH-heteroaryl, $SO_2$—$C_1$-$C_6$-alkyl, $SO_2$-aryl, $SO_2$-heteroaryl, $SO_2NH_2$, $SO_2NH$—$C_1$-$C_6$-alkyl, $SO_2NH$-aryl, $SO_2NH$-heteroaryl, $C_1$-$C_6$-alkyl, $C_3$-$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$-$C_6$-alkyl-thio, or methylthiomethyl.

The term "substituted cycloalkyl," as used herein, refers to a $C_3$-$C_7$ cycloalkyl group, as defined above, substituted by independent replacement of one or more of the hydrogen atoms therein with, for example, but not limited to, F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$-$C_6$-alkyl, NHCONH-aryl, NHCONH-heteroaryl, $SO_2$—$C_1$-$C_6$-alkyl, $SO_2$-aryl, $SO_2$-heteroaryl, $SO_2NH_2$, $SO_2NH$—$C_1$-$C_6$-alkyl, $SO_2NH$-aryl, $SO_2NH$-heteroaryl, $C_1$-$C_6$-alkyl, $C_3$-$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$-$C_6$-alkyl-thio, or methylthiomethyl.

"Hydroxy-protecting group," as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known. See, for example, T. H. Greene and P. G. M. Wuts, *Protective Groups in Organic Synthesis*, 3rd edition, John Wiley & Sons, New York (1999). Examples of hydroxy-protecting groups include, but are not limited to, methylthiomethyl, tert-dimethylsilyl, tert-butyldiphenylsilyl, acyl substituted with an aromatic group and the like.

The term "protected-hydroxy," refers to a hydroxy group protected with a hydroxy protecting group, as defined above, including, for example, but not limited to, benzoyl, acetyl, trimethylsilyl, triethylsilyl, methoxymethyl groups.

"Aldehyde-protecting group," as used herein, refers to an easily removable group which is known to protect an aldehyde group against undesirable reaction during synthetic procedures and to be selectively removable. The use of aldehyde-protecting groups is well known in the art for protecting aldehyde groups against undesirable reactions during a synthetic procedure and many such protecting groups are known. See, for example, T. H. Greene and P. G, M, Wuts, *Protective Groups in Organic Synthesis,* op. cit. Examples of aldehyde-protecting groups include, but are not limited to, acetals, ketals, O-substituted cyanohydrins, substituted hydrazones, imines and the like.

The term "protected aldehyde" refers to an aldehyde group protected with an aldehyde protecting group, as defined above, including, for example, but not limited to, dimethyl acetyl, 1,3-dioxolane, 1,3-dioxane and the like.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be apparent to those skilled in the art that individual solvents or mixtures thereof may be preferred for specific compounds and reaction conditions, for example, depending upon such factors as the solubility of reagents, reactivity of reagents and preferred temperature ranges. Further discussions of protogenic solvents may be found in organic chemistry textbooks or in specialized monographs, for example: *Organic Solvents Physical Properties and Methods of Purification,* 4th ed., edited by John A. Riddick et al., op. cit.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present. Further, in those cases where a bond between carbon atoms of the macrolide is a double bond both the cis and trans forms are within the scope of the invention described in this application.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs," as used herein, refers to those prodrugs of the compounds of the present invention which are, within the scope of sound medical judgment, suitable for use in contact with the tissues of humans and lower animals without undue toxicity, irritation, allergic response and the like, commensurate with a reasonable risk/reward ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel delivery Systems,* Vol. 14 of the A.C.S. Symposium Series and in Edward B. Roche, ed., *Bioreversible Carriers in Drug Design,* American Pharmaceutical Association and Pergamon Press, 1987, both of which are incorporated by reference herein.

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 $\mu$g/ml to about 0.03 $\mu$g/ml. The diluted compounds (2 $\mu$l/well) were then transferred into sterile, uninoculated CAMHB (0.2 mL) by use of a 96 fixed tip-pipetting station. The inoculum for each bacterial strain was standardized to $5 \times 10^5$ CFU/mL by optical comparison to a 0.5 McFarland turbidity standard. The plates were inoculated with 10 $\mu$l/well of adjusted bacterial inoculum. The 96 well plates were covered and incubated at 35+/−2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 $\mu$g/ml to about 0.03 $\mu$g/ml.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, powders, capsules, pills, and granules can be prepared with coatings and shells such as enteric coatings and other coatings well known in the pharmaceutical formulating art. They may optionally contain opacifying agents and can also be of a composition whereby they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from about 0.01 to about 50 mg/kg body weight or more preferably from about 0.1 to about 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of the compounds of the present invention per day in single or multiple doses.

Abbreviations

Abbreviations which have been used in the descriptions of the scheme and the examples that follow are: AIBN for azobisisobutyronitrile; Bu$_3$SnH for tributyltin hydride; CDI for carbonyldiimidazole; DBU for 1,8-diazabicyclo[5.4.0] undec-7-ene; DEAD for diethylazodicarboxylate; DMF for dimethyl formamide; DMSO for dimethyl sulfoxide, DPPA for diphenylphosphoryl azide; EtOAc for ethyl acetate; MeOH for methanol; NaN(TMS)$_2$ for sodium bis (trimethylsilyl)amide; NMO for N-methylmorpholine N-oxide; TEA for triethylamine; THF for tetrahydrofuran; TPP for triphenylphosphine; DMAP for 4-N,N-dimethylamino pyridine; TFA for trifluoroacetic acid; KHMDS for potassium bis(trimethylsilyl)amide; Ac for acetyl; Bz for benzoyl; TBAF for tetrabutyl ammonium fluoride; m-CPBA for meta-chloro perbenzoic acid; TBDMS for tert-butyl dimethyl silyl; and TBDPS for tert-butyldiphenyl silyl.

Synthetic Methods

The compounds and processes of the present invention will be better understood in connection with the following synthetic schemes which are illustrative of the methods by which the compounds of the invention may be prepared. The groups A, R1, R2, R3, R4, and $R^p$ are as defined previously unless otherwise noted below.

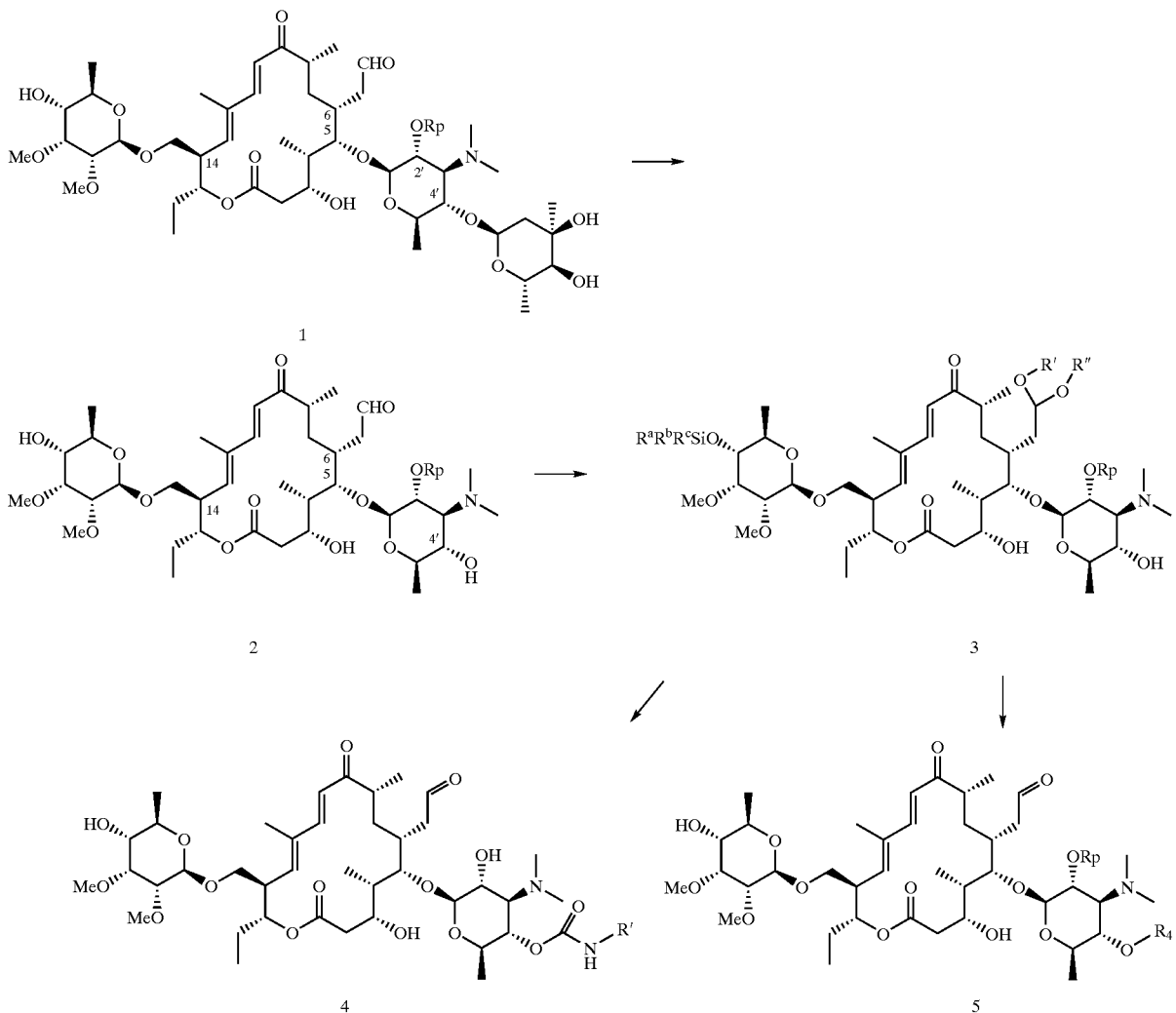

Scheme 1

One process of the invention for the preparation of the compounds of Formula I comprises treating 2'-protected tylosin (compound 1 of Scheme 1) with dilute aqueous acids (0.1–5N) such as hydrochloric acid, sulfuric acid, trifluoroacetic acid, acetic acid or the like optionally in an organic solvent such as acetone, acetonitrile, methanol, ethanol or the like or combinations thereof at from about 0° C. to about 100° C. for 1–24 hours to provide compound 2. Compound 2 is treated with acetyl chloride, hydrochloric acid, acetic acid or the like to provide a pH of 1–4 in an alcoholic solvent such as methanol, ethanol, ethylene glycol or the like to provide an acetal intermediate. The acetal intermediate is further treated with a silylating agent such as triethylsilyl chloride, TBDMSCl, TBDPSCl or the like, optionally with the addition of DMAP, imidazole or the like, in an aprotic solvent such as methylene chloride, ethylene chloride, THF, chloroform, DMF, acetonitrile or the like at from about 0° C. to about 50° C. for 1–48 hours to provide compound 3. Compound 3 is alkylated with an alkylating agent such as an alkyl halide, alkyl sulphonate, propargyl halide, allyl halide, arylallyl halide, heteroarylallyl halide, benzyl halide or the like in the presence of a base such as sodium hydride, potassium hydride, potassium tert-butoxide, potassium hydroxide, KHMDS, or the like in an aprotic solvent such as THF, DMSO, DMF, dioxane, or the like or mixtures thereof at from about −20° C. to about 60° C. to provide a protected compound 5 which can be deprotected with aqueous acid to remove the acetal protecting group and TBAF or hydrofluoric acid to remove the silyl protecting group followed by methanolysis at temperature(s) between room temperature to reflux temperature to remove the $R^p$ protecting group at the 2'-position where ORP is an ester or a silyl ether to provide compound 5. Compound 3 can also be treated with an isocyanate reagent, optionally adding triethylamine, DMAP, imidazole or the like, in an aprotic organic solvent such as methylene chloride, ethylene chloride, THF, chloroform, DMF, acetonitrile or the like at from about 0° C. to about 50° C. for 1–48 hours followed by deprotection of the protecting groups to provide compound 4.

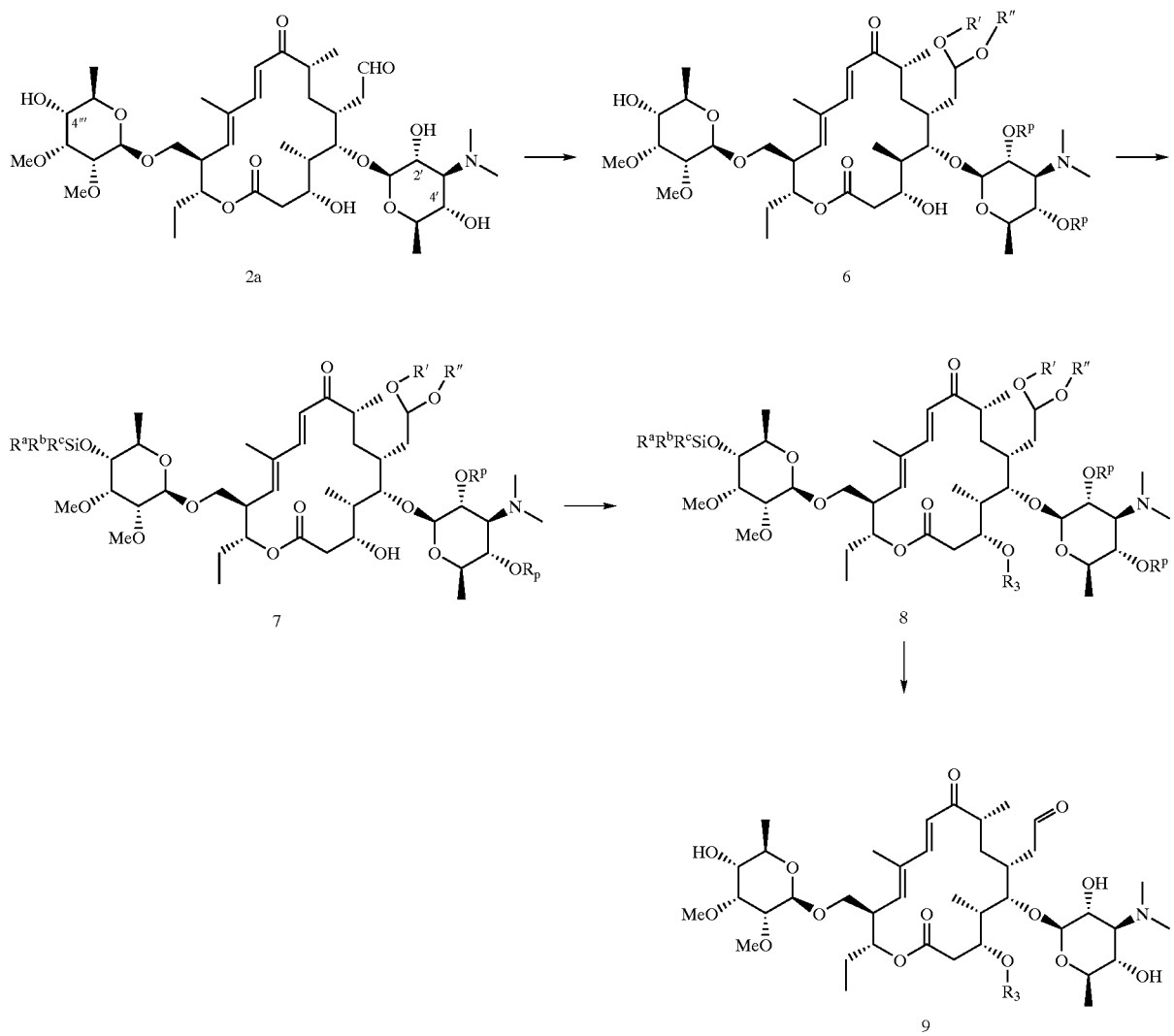

In another process of the invention, for the preparation of the compounds of Formula I, desmycosin (compound 2a of Scheme 2) is treated with acetyl chloride, hydrochloric acid, acetic acid or the like to provide a pH of 1–4 in an alcoholic solvent such as methanol, ethanol, ethylene glycol or the like to protect the aldehyde as an acetal followed by the protection of each of the 2'- and 4'-hydroxyl groups as an ester or a silyl protection group by reacting with the corresponding acid anhydride or silylating reagent such as silyl chloride, HMDS, BSA and the like in an aprotic solvent such as methylene chloride, ethylene chloride, THF, chloroform, DMF, acetonitrile or the like at from about 0° C. to about 50° C. for 1–48 hours to provide compound 6. Compound 6 is further selectively protected with a silyl protecting group by reacting with a silyl chloride reagent optionally in the presence of an additive such as DMAP, imidazole, triethylamine and the like, in an aprotic solvent such as methylene chloride, ethylene chloride, THF, chloroform, DMF, acetonitrile or the like at from about 0° C. to about 50° C. for 1–48 hours to provide compound 7. Compound 7 is alkylated with an alkylating agent such as an alkyl halide, alkyl sulphonate, propargyl halide, allyl halide, arylallyl halide, heteroaryla-llyl halide, benzylic halide or the like in the presence of a base such as sodium hydride, potassium hydride, potassium tert-butoxide, potassium hydroxide, KHMDS, or the like in an aprotic solvent such as THF, DMSO, DMF, dioxane, or the like or mixtures there of at from about −20° C. to about 60° C. to provide a protected compound 8 which can be deprotected with aqueous acid to remove the acetal protecting group and TBAF or hydrofluoric acid to remove the silyl protecting group followed by methanolysis at temperature(s) between room temperature to reflux temperature to remove the $R^P$ protecting group at the 2'- and 4'-positions where $OR^P$ is an ester or a silyl ether to provide compound 9.

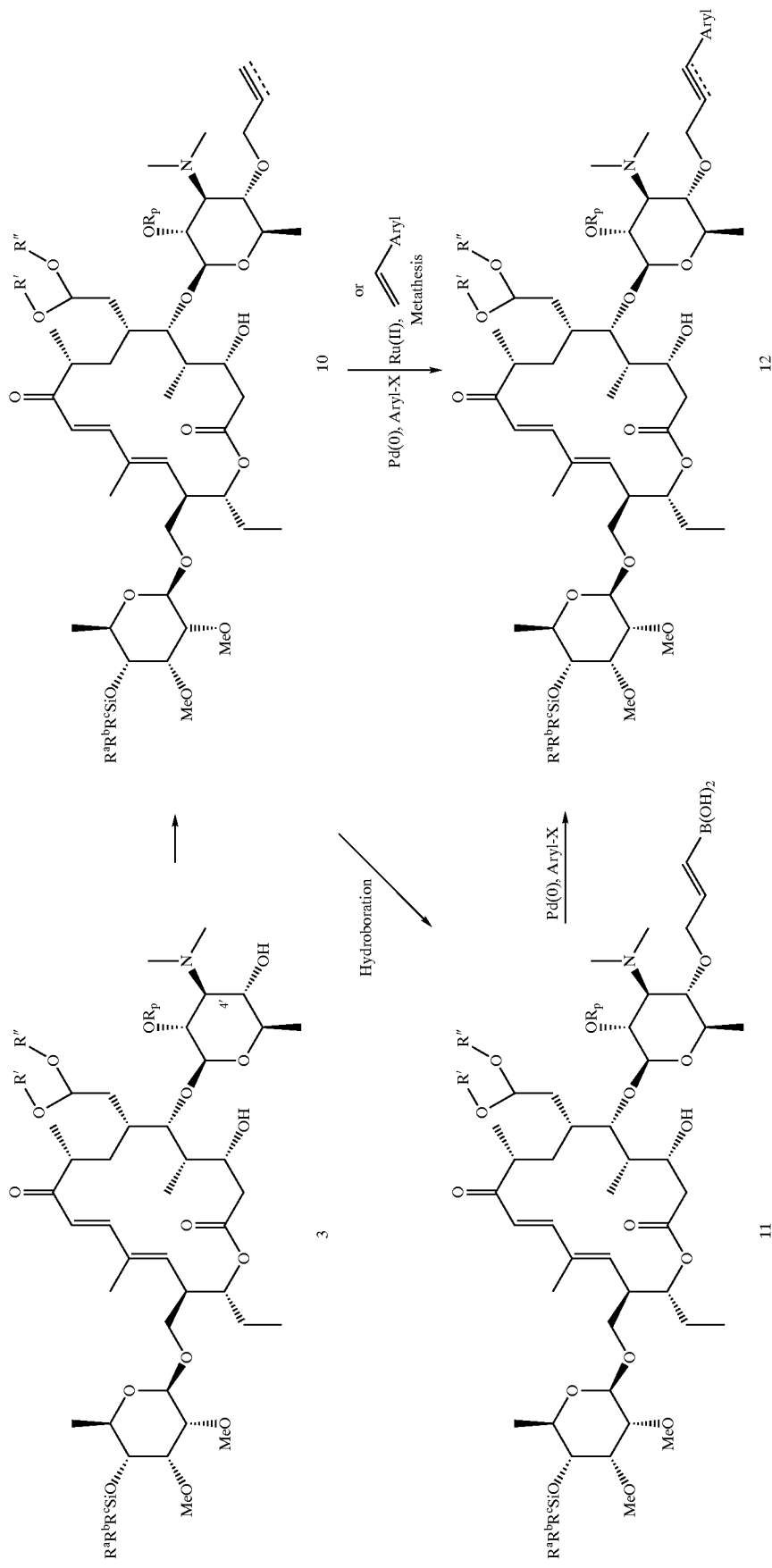

In yet another process of the invention for the preparation of the compounds of Formula I, compound 3 of Scheme 1 is reacted with an allyl bromide or propargyl bromide as described above in Scheme 1 to provide compound 10. Compound 10 is treated with an aryl halide or aryl triflate in the presence of a palladium catalyst [Pd(0) or Pd(II)] to provide compound 12: (See (a) Heck, Palladium Reagents in Organic Synthesis, Academic Press: New York, 1985, Chapter 1; (b) Sonogashira, Comprehensive Organic Synthesis, Volume 3, Chapters 2, 4; (c) Sonogashira, *Synthesis* 1977, 777). Under the Heck coupling conditions, region-isomers and stereo-isomers of the double bond are possible. Alternatively, compound 10 can undergo a cross metathesis reaction with vinylaromatic derivatives using ruthenium catalysts to provide compound 12 (see (a) *J. Org. Chem.* 2000, 65, 2204–2207; (b) Reviews: *Synlett.* 1999, 2, 267; (c) Reviews: Ivin, K. J.; Mol, J. C. *Olefin Metathesis and Metathesis Polymerization*, $2^{nd}$ ed.; Academic Press: New York, 1997; (d) *J. Org. Chem.* 1999, 64, 4798–4816; (e) *Angew. Chem., Int. Ed. Engl.* 1997, 36, 2036–2056; (f) *Tetrahedron* 1998, 54, 4413–4450). Alternatively, the propargyl group of compound 10 is reduced with a variety of borane reagents to give vinyl boronic acid 11 for further palladium catalyzed Suzuki coupling reactions to provide compound 12 (see (a) Suzuki, Chemical Reviews, 1995, 95, 2457; (b) Suzuki, *Pure & Appl. Chem.* 1991, 63, 419). Compound 12 is further deprotected as described earlier to provide 4'-ether compounds of Formula I.

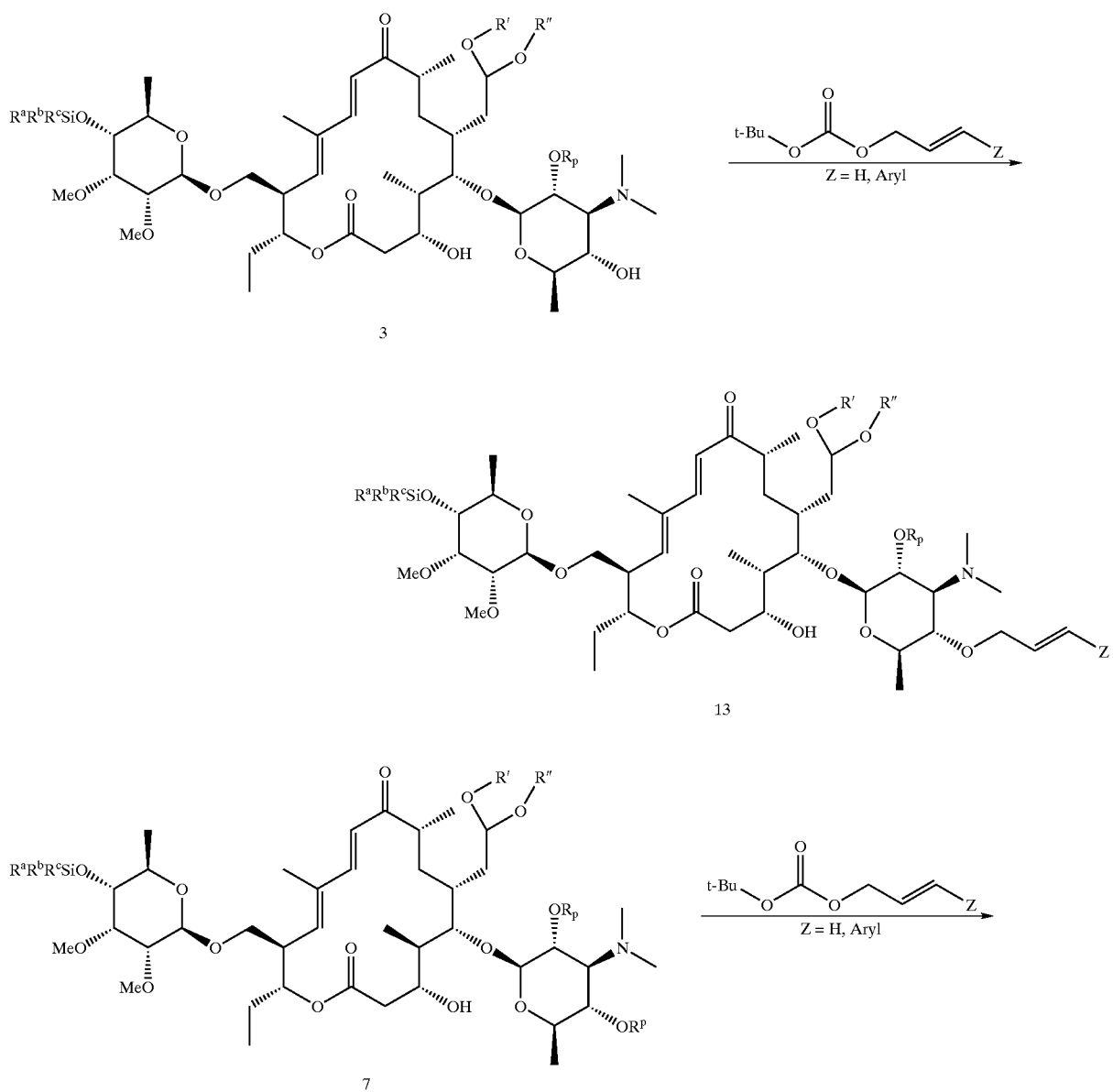

Scheme 4

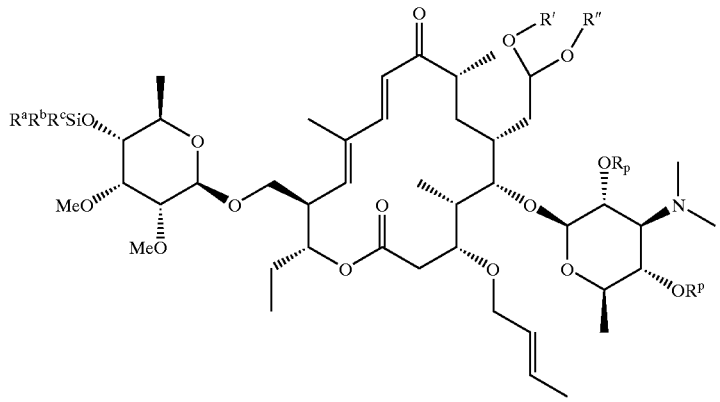

14

In yet another process of the invention for the preparation of the compounds of Formula I, compound 3 of Scheme 1 is reacted with a tert-butyl allyl carbonate or a tert-butyl aryl allyl carbonate catalyzed by a palladium catalyst [Pd(0) or Pd(II)] to provide compound 13 directly: (See (a) Trost, B. M. *Angew. Chem. Int. Ed. Eng.* 1989, 28, 1179. (b) Heck, Palladium Reagents in Organic Synthesis, Academic Press: New York, 1985, Chapter 1. (c) Tsuji Tetrahedron Lett. 1992, 33, 2987). Similarly compound 7 can undergo the same palladium catalyzed allylation with allyl carbonate reagents to provide compound 14. Compounds 13 and 14 are deprotected as above to provide compounds of Formula I.

Compounds of Formula I where A is an aldehyde, for example, but not limited to, an intermediate derived from compound 8 with the aldehyde protecting group removed by aqueous acid or compounds 4 or 5, can be further derivatized into other derivatives by reduction of the aldehyde to provide an alcohol which can be further converted into a halogen by standard chemical methods. When A is an aldehyde, it can be further converted into an oxime or hydrazone moiety by treatment with the corresponding hydroxylamine or hydrazine. The unsubstituted oxime moiety can be derivatized into a leaving group and can be further converted into a nitrile upon treatment with a mild base, such as a trialkyl amine. Also, when A is an aldehyde the aldehyde functionality can be condensed with various amino derivatives to form heteroaromatic or substituted heteroaromatic moieties.

EXAMPLES

The procedures described above for preparing the compounds of Formula I of the present invention will be better understood in connection with the following examples which are intended to be illustrative only of, and not limiting of the scope of the invention. Various changes and modifications to the disclosed embodiments will be apparent to those skilled in the art. Such changes and modifications, including without limitation, those relating to the chemical structures, substituents, derivatives, syntheses, formulations and/or methods of the invention may be made without departing from the spirit of the invention and the scope of the appended claims.

Example 1

Compound of Formula I: A=—CHO, R1 and R2 Taken Together=O, R3=H, R4=—CH$_2$CHCH$_2$ and R$^P$=H Step 1a. Compound 1 of Scheme 1: R$^P$=acetyl To a solution of tylosin (45.8 g, 05 mol) in acetone (100 mL) was added acetic anhydride (25 mL) at room temperature for 2 hours. The solvent was evaporated under vacuum, then chased with toluene (30 mL×3) to give the title compound (48 g, 100%).

MS (ESI) m/z 958 (M+H)$^+$.

Step 1b. Compound of Formula I: A=2-(1,3-dioxolane), R1 and R2 Taken Together=O, R3=H, R4=H and R$^P$=Acetyl A solution of p-toluenesulfonic acid monohydrate (0.95 g, 5 mmol), ethylene glycol (5 mL), and benzene (5 mL) was charged into a round bottom flask, equipped with Dean-stark and condenser. The reaction was refluxed for 4 hours. After the reaction was cooled to room temperature, the reaction mixture was poured into a solution of the compound from step 1a (4.8 g, 5 mmol) in acetonitrile (5 mL). The reaction was stirred at room temperature for 16 hours. The solvent was evaporated under vacuum. The residue was extracted with dichloromethane, washed with saturated aqueous NaHCO$_3$, and dried over anhydrous Na$_2$SO$_4$. The solvent was evaporated to give the title compound (3.6 g, 84%).

MS (ESI) m/z 858 (M+H)$^+$.

Step 1c. Compound 3 of Scheme 3: R' and R" Taken Together=—CH$_2$—CH$_2$—, R$^a$R$^b$R$^c$Si=TBDPS, and R$^P$=acetyl To a solution of the compound from step 1b (1.29 g, 1.5 mmol) in DMF (3 mL) was added imidazole (0.12 g, 1.8 mmol) and tert-butyldiphenylsilyl chloride (0.29 mL, 1.65 mmol). The mixture was stirred at room temperature for 16 hours. The solvent was evaporated under vacuum. Purification on a silica gel column (eluting with acetone:hexane/1:4) gave the title compound (1.25 g, 76%) as a white solid.

MS (ESI) m/z 1096 (M+H)$^+$.

$^{13}$C-NMR (100 MHz, CDCl$_3$): δ203.6, 173.7, 169.4, 136.2, 134.9, 133.9, 133.5, 130.1, 127.9, 127.8, 104.1, 102.5, 101.1, 81.8, 79.9, 75.6, 75.2, 73.1, 70.8, 70.7, 69.8, 68.6, 64.8, 64.7, 61.3, 59.3, 45.1, 41.5, 39.8, 32.8, 27.3, 26.7, 5.4, 21.8, 19.6, 18.4, 18.0, 13.2, 9.9, 8.9.

Step 1d. Compound 10 of Scheme 3: R' and R" Taken Together=—CH$_2$—CH$_2$—, R$^a$R$^b$R$^c$Si=TBDPS, and R$^P$=acetyl A solution of the compound from step 1c (0.767 g, 0.7 mmol), t-butyl allylcarbonate (0.332 g, 2.1 mmol), 1,4-bis (diphenylphosphino)butane (59.7 mg, 0.14 mmol), tris (dibenzylideneacetone)dipalladium (64.1 mg, 0.07 mmol) in degassed THF (4 mL) was heated at 68° C. for 4 hours and concentrated. Purification on silica gel column (eluting with ethyl acetate:hexane/1:4, then acetone:hexane/1:4) gave the title compound (200 mg, 25%) as a white solid.

MS (ESI) m/z 1136 (M+H)$^+$.

$^{13}$C-NMR (100 MHz, CDCl$_3$): δ203.4, 173.8, 169.7, 136.2, 135.2, 134.9, 133.9, 133.4, 130.1, 127.9, 127.8, 117.1, 104.1, 102.3, 101.1, 81.8, 79.9, 79.7, 75.6, 75.2, 73.3, 72.5, 71.1, 69.8, 69.2, 64.8, 64.6, 61.3, 59.3, 45.1, 41.7, 32.9, 27.3, 21.7, 19.7, 18.4, 18.2, 13.2, 9.9, 8.9.

Step 1e. Compound of Formula 1: A=2-(1,3-dioxolane), R1 and R2 Taken Together=O, R3=H, R4=—CH$_2$CHCH$_2$ and R$^P$=acetyl To a solution of the compound from step 1d (180 mg, 0.16 mmol) in THF (1 mL) was added tetrabutylammonium fluoride (0.8 mL, 1.0 M in THF). The mixture was stirred at room temperature for 1 hour. The solvent was evaporated under vacuum, and the residue was extracted with dichloromethane, washed with water, dried over anhydrous Na$_2$SO$_4$. The solvent was evaporated under vacuum to give the title compound.

MS (ESI) m/z 898 (M+H)$^+$.

Step 1f. Compound of Formula I: A=—CHO, R1 and R2 Taken Together=O, R3=H, R4=—CH$_2$CHCH$_2$ and R$^P$=acetyl To a solution of the compound from step 1e in CH$_3$CN (1 mL) was added 0.3 N aqueous HCl solution (4 mL). The mixture was stirred for 1 hour at room temperature, neutralized with saturated aqueous NaHCO$_3$ and extracted with dichloromethane. The organic solution was dried over anhydrous Na$_2$SO$_4$, and concentrated under vacuum. Purification on silica gel column (eluting with acetone:hexane/1:4) gave the title compound (90 mg, 67%) as a white solid.

MS (ESI) m/z 854 (M+H)$^+$.

Step 1g. Compound of Formula I: A=—CHO, R1 and R2 Taken Together=O, R3=H, R4=—CH$_2$CHCH$_2$ and R$^P$=H A solution of the compound from step 1f (90 mg, 0.11 mmol) in methanol (2 mL) was stirred for 16 hours at room temperature. The solvent was evaporated under vacuum to give the title compound (80 mg, 100%) as a white solid.

MS (ESI) m/z 812 (M+H)$^+$.

$^{13}$C-NMR (100 MHz, CDCl$_3$): δ202.4, 202.2, 172.8, 147.1, 141.1, 138.3, 133.8, 133.3, 116.1, 113.1, 102.6, 100.9, 80.9, 78.8, 78.6, 73.9, 72.1, 71.6, 71.3, 69.6, 69.1, 68.7, 60.8, 58.8, 44.1, 40.5, 40.0, 32.8, 30.9, 29.3, 27.9, 21.7, 17.1, 16.8, 16.5, 13.1, 11.9, 8.6, 7.7.

Example 2

Compound of Formula I: A=CHO, R1 and R2 Taken Together=O, R3=—CH$_2$CHCH$_2$, R4=H and R$^P$=H Step 2a. Compound of Formula I: A=—CHO, R1 and R2 Taken Together=O, R3=H, R4=H and R$^P$=H A solution of tylosin (40 g, 44 mmol) in 0.3N HCl (200 mL) was stirred for 2 hours at room temperature, neutralized with saturated aqueous NaHCO$_3$ and extracted with dichloromethane. The organic solution was dried over anhydrous Na$_2$SO$_4$, and concentrated under vacuum to give the title compound (32.7 g, 97%).

MS (ESI) m/z 772 (M+H)$^+$.

$^{13}$C-NMR (100 MHz, CDCl$_3$): δ203.3, 203.2, 174.0, 148,2, 142.5, 135.0, 101.2, 82.0, 80.0, 75.2, 73.5, 72.9, 71.1, 71.0, 70.7, 70.3, 69.2, 61.9, 59.7, 53.6, 45.2, 44.9, 43.9, 41.9, 39.5, 25.6, 18.0, 17.9, 17.6, 13.1, 9.8, 9.1.

Step 2b. Compound of Formula I: A=—CHO, R1 and R2 Taken Together=O, R3=H, R4=Acetyl and R$^P$=acetyl To a solution of the compound from step 2a (32.7 g, 0.44 mol) in acetone (100 mL) was added acetic anhydride (25 mL) at room temperature for 2 hours. The solvent was evaporated under vacuum. The residue was extracted with dichloromethane, washed with saturated aqueous NaHCO$_3$.

The organic solution was dried over anhydrous Na$_2$SO4, and concentrated under vacuum to give the title compound (36.6 g, 100%).

MS (ESI) m/z 856 (M+H)$^+$.

$^{13}$C-NMR (100 MHz, CDCl$_3$): δ203.3, 203.2, 173.9, 169.9, 169.4, 166.5, 148.1, 142.4, 134.9, 118.3, 101.9, 101.2, 81.9, 80.9, 80.0, 75.2, 72.9, 71.5, 71.1, 70.6, 69.1, 67.2, 66.8, 61.9, 60.5, 59.8, 45.1, 43.7, 41.3, 40.9, 39.4, 31.8, 31.2, 25.4, 22.2, 21.4, 21.3, 21.1, 17.9, 17.6, 17.3, 14.3, 13.2, 9.8, 8.7.

Step 2c. Compound of Formula I: A=2-(1,3-dioxolane), R1 and R2 Taken Together=O, R3=H, R4=Acetyl and R$^P$=acetyl To a solution of the compound from step 2b (36 g, 42 mmol) in methanol (100 mL) was added acetic chloride (3.6 mL, 50 mmol) at 0° C. The mixture was stirred for 1 hour, neutralized with triethylamine (5.5 mL, 74 mmol) and concentrated. The residue was dissolved in ethyl acetate, washed with saturated aqueous NaHCO$_3$ and water. The organic solution was dried over anhydrous Na$_2$SO$_4$ and concentrated under vacuum to provide the title compound (37 g, 98%).

MS (ESI) m/z 902 (M+H)$^+$.

$^{13}$C-NMR (100 MHz, CDCl$_3$): δ203.8, 173.8, 171.2, 169.9, 169.4, 147.6, 142.3, 134.9, 102.6, 102.3, 101.2, 82.0, 81.5, 80.0, 75.2, 72.8, 71.7, 71.1, 70.8, 69.2, 67.4, 67.0, 61.9, 60.5, 59.8, 53.7, 50.0, 45.2, 41.4, 39.9, 32.8, 31.1, 25.4, 21.5, 21.4, 21.2, 17.9, 17.3, 14.3, 13.2, 9.8, 8.8.

Step 2d. Compound 7 of Scheme 2: R' and R" Each=—CH$_3$, R$^a$R$^b$R$^3$Si=triethylsilyl and R$^P$=acetyl To a solution of the compound from step 2c (9.9 g, 11 mmol) in dichloromethane (55 mL) was added DMAP (0.34 g, 2.7 mmol), triethylamine (2.3 mL, 16.5 mmol), chlorotriethylsilane (2.0 mL, 12.1 mmol) at 0° C. The mixture was stirred for 2 hours, and concentrated. The residue was dissolved in ethyl acetate, washed with saturated aqueous NaHCO$_3$ and water. The organic solution was dried over anhydrous Na$_2$SO$_4$ and concentrated under vacuum. Purification on silica gel column (eluting with acetone:hexane/ 1:4) gave the title compound (10 g, 90%) as a white solid.

MS (ESI) m/z 684 (M+H)$^+$.

$^{13}$C-NMR (100 MHz, CDCl$_3$): δ203.8, 173.8, 169.9, 169.4, 147.7, 142.3, 134.8, 102.7, 102.3, 101.3, 81.6, 81.4, 81.2, 75.2, 71.7, 71.2, 70.8, 69.7, 69.1, 67.5, 67.9, 61.8, 59.7, 53.7, 50.1, 45.2, 41.4, 39.9, 33.1, 32.8, 29.8, 25.4, 21.5, 21.4, 17.9, 17.4, 13.2, 9.9, 8.9, 7.0, 5.1.

Step 2e. Compound 8 of Scheme 2: R' and R" Each=—CH$_3$, R$^a$R$^b$R$^c$Si=triethylsilyl, R3=—CH$_2$CHCH$_2$ and R$^P$=Acetyl A solution of the compound from step 2d (3.0 g, 3 mmol), t-butyl allylcarbonate (1.9g, 12mmol), 1,4-bis (diphenylphosphino)butane (0.256 g, 0.6 mmol), tris (dibenzylideneacetone)dipalladium (0.275 g, 0.3 mmol) in degassed THF (20 mL) was heated at 68° C. for 16 hours and concentrated. Purification on silica gel column (eluting with ethyl acetate:hexane/1:4) gave the title compound (1.2 g, 38%) as a white solid.

MS (ESI) m/z 1136 (M+H)$^+$.

$^{13}$C-NMR (100 MHz, CDCl$_3$): δ203.4, 171.9, 169.9, 169.4, 147.6, 142.6, 135.9, 134.3, 115.2, 102.2, 101.3, 100.1, 81.3, 81.2, 78.8, 75.8, 71.8, 71.6, 71.0, 70.6, 69.3, 67.4, 61.8, 59.8, 53.8, 49.6, 45.1, 44.2, 41.4, 39.5, 36.7, 34.8, 33.0, 31.7, 25.4, 21.5, 21.4, 17.9, 17.5, 12.9, 9.8, 9.2, 7.0, 5.1.

Step 2f. Compound of Formula I: A =—CHO, R1 and R2 Taken Together=O, R3=—CH$_2$CHCH$_2$, R4=acetyl and R$^P$=acetyl To a solution of the compound from step 2e (100 mg, 0.09 mmol) in CH$_3$CN (2 mL) was added 1 N HCl aqueous solution (2 mL). The mixture was stirred for 20 minutes at room temperature, neutralized with saturated aqueous NaHCO$_3$ and extracted with dichloromethane. The organic solution was dried over anhydrous Na$_2$SO$_4$ and concentrated under vacuum. Purification on silica gel column (eluting with acetone:hexane/1:4) gave the title compound (65 mg, 76%) as a white solid.

MS (ESI) m/z 896(M+H)$^+$.

Step 2g. Compound of Formula I: A=—CHO, R1 and R2 Taken Together=O, R3=H, R4=—CHCHCH$_2$—(3-quinolyl) and R$^P$=Acetyl A solution of the compound from step 2f (65 mg, 0.07 mmol) in methanol (2 mL) was stirred for 16 hours at room temperature. The solvent was evaporated under vacuum to give the title compound (58 mg, 100%) as a white solid.

MS (ESI) m/z 812 (M+H)$^+$.

$^{13}$C-NMR (100 MHz, CDCl$_3$): δ203.5, 202.2, 171.8, 148.4, 143.1, 135.5, 134.3, 118.7, 116.0, 103.1, 101.3, 82.0, 79.9, 79.3, 76.1, 75.2, 73.4, 72.8, 71.9, 71.4, 70.9, 70.8, 70.3, 61.9, 59.9, 45.1, 45.0, 44.3, 43.6, 41.9, 39.2, 35.3, 29.9, 25.5, 18.0, 17.9, 17.7, 13.0, 9.8, 9.7.

Example 3

Compound of Formula I: A=—CHO, R1 and R2 Taken Together=O, R3=H, R4=——CHCHCH$_2$— (3-quinolyl) and R$^P$=H Step 3a. Compound of Formula I: A=—CHO, R1 and R2 Taken Together=O, R3=H, R4=—CHCHCH$_2$-(3-quinolyl) and R$^P$=acetyl A solution of the compound from step 1f (80 mg, 0.09 mmol), 3-bromoquinoline (39 mg, 0.187 mmol), tri-o-tolylphosphine (8.6 mg, 0.028 mmol), triethylamine (23.7 mg, 0.23 mmol), and palladium (II) acetate (3.15 mg, 0.014 mmol) in degassed acetonitrile (0.9 mL) was heated at 80° C. for 16 hours and concentrated. Purification on a silica gel column (eluting with acetone:hexane/1:4) gave a major amount of the title compound (46 mg, 50%) and a minor amount of a compound which was the same as the title compound except that R4=CH$_2$CHCH-(3-quinolyl).

MS (ESI) m/z 981 (M+H)$^+$.

Step 3b. Compound of Formula I: A=—CHO, R1 and R2 Taken Together=O, R3=H, R4=—CHCHCH2-(3-quinolyl) and R$^P$=H A solution of the title compound from step 3a (46 mg) in methanol (2 mL) was stirred for 16 hours at room temperature. The solvent was evaporated under vacuum. Purification on silica gel column (eluting with acetone:hexane/1:3) gave the title compound (12 mg, 27%).

MS (ESI) m/z 939 (M+H)$^+$.

$^3$C-NMR (100 MHz, CDCl$_3$): δ203.5, 203.3, 174.0, 152.1, 148.3, 146.9, 146.5, 142.6, 1135.0, 134.1, 134.0, 129.3, 128.8, 128.3, 127.4, 126.8, 118.3, 103.8, 103.7, 101.3, 82.5, 82.1, 81.8, 80.0, 75.2, 72.8, 72.6, 70.8, 69.8, 69.7, 69.2, 61.9, 59.9, 45.3, 43.9, 41.7, 41.1, 39.7, 31.8, 27.9, 25.5, 22.8, 17.9, 17.7, 14.4, 13.1, 9.8, 8.9.

Example 4

Compound of Formula I: A=—CHO, R1 and R2 Taken Together=O, R3=H, R4=—CH$_2$CHCH-(3-quinolyl) and R$^P$=H The compound which was obtained in a minor amount in step 3a of Example 3 was treated with methanol in accordance with the procedure described in step 3b to provide the title compound.

MS (ESI) m/z 939 (M+H)$^+$.

$^3$C-NMR (100 MHz, CDCl$_3$): δ203.6, 203.4, 174.0, 149.3, 148.3, 147.7, 142.6, 135.0, 132.9, 129.6, 129.5, 129.4, 128.9, 127.2, 103.8, 101.3, 82.1, 80.0, 79.9, 75.2, 73.2, 72.8, 71.9, 70.8, 70.4, 69.9, 69.6, 69.1, 61.9, 59.9, 54.0, 45.3, 45.2, 43.9, 41.9, 39.7, 31.9, 25.5, 18.4, 17.9, 17.7, 13.1, 9.8, 8.9.

Example 5

Compound of Formula I: A=—CHO, R1 and R2 Taken Together=O, R3 =—CH$_2$CHCH-phenyl, R4= H and R$^P$=H Step 5a. Compound 14 of Scheme 4: R' and R" Each=CH$_3$, R$^a$R$^b$R$^c$Si=triethylsilyl, Z=phenyl and R$^P$=acetyl To a solution of the compound from step 2e (200 mg, 0.2 mmol) in dichloromethane (2 mL) was added styrene (62.4 mg, 0.6 mmol), and bis(tricyclohexylphosphine)benzylidine ruthenium(IV) dichloride (Grubbs's catalyst) (16.5 mg, 0.02 mmol). The mixture was refluxed for 3 hours, diluted with dichloromethane, and washed with saturated aqueous NaHCO$_3$. The organic solution was dried over anhydrous Na$_2$SO$_4$ and concentrated under vacuum. Purification on a silica gel column (eluting with acetone:hexane/1:4) gave the title compound (186 mg, 82%) as a white solid.

MS (ESI) m/z 1132 M+H)$^+$.

Step 5b. Compound of Formula I: A=—CHO, R1 and R2 Taken Together=O, R3=—CH$_2$CHCH-phenyl, R4=acetyl and R$^P$=acetyl To a solution of the compound from step 5a (186 mg, 0.16 mmol) in CH$_3$CN (3 mL) was added 1 N aqueous HCl solution (3 mL). The mixture was stirred for 20 minutes at room temperature, neutralized with saturated aqueous NaHCO$_3$ and extracted with dichloromethane. The organic solution was dried over anhydrous Na$_2$SO$_4$ and concentrated under vacuum. Purification on a silica gel column (eluting with acetone:hexane/1:4) gave the title compound (75 mg, 47%).

MS (ESI) m/z 972(M+H)$^+$.

Step 5c. Compound of Formula I: A=—CHO, R1 and R2 Taken Together=O, R3=—CH$_2$CHCH-phenyl, R4=H and R$^P$=H A solution of the compound from step 5b (75 mg) in methanol (3 mL) was stirred for 16 hours at room temperature. The solvent was evaporated under vacuum to give the title compound (54 mg, 92%).

MS (ESI) m/z 888 (M+H)$^+$.

$^{13}$C-NMR (100 MHz, CDCl$_3$): δ203.6, 202.0, 171.8, 148.3, 143.1, 137.0, 134.3, 131.7, 131.7, 128.7, 127.7, 126.9, 126.6, 118.8, 103.3, 101.3, 82.0, 79.9, 79.8, 76.5, 75.2, 73.4, 72.8, 71.8, 71.3, 70.8, 70.3, 69.4, 61.9, 59.9, 45.1, 45.0, 44.4, 43.6, 41.8, 39.2, 35.4, 32.5, 25.5, 18.0, 17.9, 17.7, 12.9, 9.8.

Example 6

Compound of Formula I: A=—CHO, R1 and R2 Taken Together=O, R3=—CHCHCH$_2$-(3-quinolyl), R4=H and R$^P$=H Step 6a Compound of Formula I: A=—CHO, R1 and R2 taken together=O, R3=—CHCHCH$_2$-(3-quinolyl), R4=acetyl and R$^P$=acetyl A solution of the compound from step 2f (135 mg, 0.15 mmol), 3-bromoquinoline (62.4 mg, 0.3 mmol), tri-o-tolyphosphine (13.7 mg, 0.045 mmol), triethyl amine (37.9 mg, 0.38 mmol) and palladium (II) acetate (5.1 mg, 0.025 mmol) in degassed acetonitrile (1.0 mL) was heated at 80° C. for 16 hours and concentrated. Purification on a silica gel column (eluting with acetone:hexane/1:3) gave a major amount of the title compound (93 mg, 60%) and a minor amount of a compound which was the same as the title compound except that R3=CH$_2$CHCH-(3-quinolyl).

MS (ESI) m/z 1023 (M+H)$^+$.

Step 6b. Compound of Formula I: A=—CHO, R1 and R2 Taken Together=O, R3=—CHCHCH$_2$-(3-quinolyl), R4=H and R$^P$=H A solution of the title compound from step 6a (93 mg) in methanol (3 mL) was stirred for 16 hours at room temperature. The solvent was evaporated under vacuum. Purification on a silica gel column (eluting with dichloromethane:methanol/10:1) gave the title compound (50 mg, 58%).

MS (ESI) m/z 939 (M+H)$^+$.

Example 7

Compound of Formula I; A=—CHO, R1 and R2 Taken Together=O, R3=—CH$_2$CHCH-(3-quinolyl), R4=H and R$^P$=H The compound which was obtained in a minor amount in step 6a of Example 6 is treated with methanol in accordance with the procedure described in step 6b to provide the title compound.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound represented by Formula I, or a pharmaceutically acceptable salt, ester or prodrug thereof:

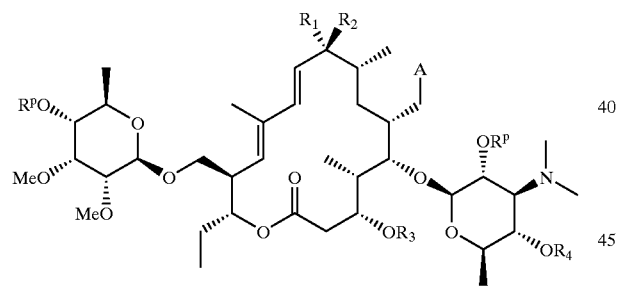

(I)

wherein
A is selected from the group consisting of:
(1) —CHO or a protected aldehyde;
(2) —CH$_2$X, wherein X is selected from the group consisting of:
  a. hydroxy or protected hydroxyl; and
  b. halogen;
(3) —CN;
(4) —CH=N—NR7R8, wherein R7 and R8 are each independently selected from the group consisting of hydrogen; C1–C6-alkyl, optionally substituted with one or more substituents selected from the group consisting of halogen, aryl, substituted aryl, heterocyclic and substituted heterocyclic; C2–C6-alkenyl, optionally substituted with one or more substituents selected from the group consisting of halogen, aryl, substituted aryl, heterocyclic and substituted heterocyclic; and C2–C6-alkynyl, optionally substituted with one or more substituents selected from the group consisting of halogen, aryl, substituted aryl, heterocyclic and substituted heterocyclic; or wherein R7R8, taken with the nitrogen atom to which they are connected, form a 3- to 7-membered ring which may optionally contain a hetero-function selected from the group consisting of —O—, —NH—, —N(C1–C6-alkyl)-, —N(aryl)-, —N(heteroaryl)-, —S—, —S(O)— and —S(O)$_2$—;
(5) —CH=N—OR7, wherein R7 is as previously defined;
(6) substituted or unsubstituted imidazole, arylimidazole or heteroarylimidazole;
(7) substituted or unsubstituted oxazole, aryloxazole or heteroaryloxazole, substituted or unsubstituted thioxazole, arylthioxazole or heteroarylthioxazole;
(8) substituted or unsubstituted imidazoline, arylimidazoline or heteroarylimidazoline;
(9) substituted or unsubstituted oxazoline, aryloxazoline or heteroaryloxazoline; and
(10) substituted or unsubstituted thioxazoline, arylthioxazoline and heteroarylthioxazoline;

R1 and R2 are each independently selected from the group consisting of:
(1) hydrogen;
(2) hydroxyl;
(3) protected hydroxyl;
(4) —OC(O)—C1–C12-alkyl, optionally substituted with one or more substituents selected from the group consisting of halogen, aryl, substituted aryl, heterocyclic, substituted heterocyclic, O—R7 and NR7R8, where R7 and R8 are as previously defined;
(5) —O—R7, where R7 is as previously defined;
(6) halogen;
(7) —NR7R8, where R7 and R8 are as previously defined; and
(8) R1 and R2 taken together are oxo;

R3 is selected from the group consisting of:
(1) hydrogen;
(2) a hydroxy protecting group;
(3) —C(O)—C1–C12-alkyl, optionally substituted with one or more substituents selected from the group consisting of halogen, aryl, substituted aryl, heterocyclic, substituted heterocyclic, O—R7 and NR7R8, where R7 and R8 are as previously defined;
(4) C1–C6-alkyl, optionally substituted with one or more substituents selected from the group consisting of halogen, aryl, substituted aryl, heterocyclic, substituted heterocyclic, O—R7 and NR7R8, where R7 and R8 are as previously defined;
(5) C2–C6-alkenyl, optionally substituted with one or more substituents selected from the group consisting of halogen, aryl, substituted aryl, heterocyclic, substituted heterocyclic, O—R7 and NR7R8, where R7 and R8 are as previously defined; and
(6) C2–C6-alkynyl, optionally substituted with one or more substitutents selected from the group consisting of halogen, aryl, substituted aryl, heterocyclic, substituted heterocyclic, O—R7 and NR7R8, where R7 and R8 are as previously defined;

R4 is —M—Y,
where M is:
(1) absent,
(2) —C(O)N(R7)-, where R7 is as previously defined,
(3) —C1–C6-alkyl-N(R7)-, where R7 is as previously defined,
(4) —C2–C6-alkenyl-N(R7)-, where R7 is as previously defined, or (5) —C2–C6-alkynyl-N(R7)-, where R7 is as previously defined;
and where Y is:
(1) hydrogen,
(2) hydroxy protecting group,
(3) C1–C6-alkyl, optionally substituted with one or more substituents selected from the group consisting of halogen, aryl, substituted aryl, heterocyclic, substituted heterocyclic and —OR7, where R7 is as previously defined,
(4) C2–C6-alkenyl, optionally substituted with one or more substituents selected from the group consisting of halogen, aryl, substituted aryl, heterocyclic, substituted heterocyclic and —OR7, where R7 is as previously defined,
(5) C2–C6-alkynyl, optionally substituted with one or more substituents selected from the group consisting of halogen, aryl, substituted aryl, heterocyclic, substituted heterocyclic and —OR7, where R7 is as previously defined,
(6) aryl,
(7) substituted aryl,
(8) heterocyclic, or
(9) substituted heterocyclic; and
$R^P$ is hydrogen or a hydroxy protecting group;
provided that when R3 is hydrogen and M is absent, Y is not hydrogen.

2. A compound according to claim 1, wherein R3 is selected from the group consisting of:
(1) C1–C6-alkyl, optionally substituted with one or more substituents selected from the group consisting of halogen, aryl, substituted aryl, heterocyclic, substituted heterocyclic, O—R7 and NR7R8, where R7 and R8 are as defined in claim 1;
(2) C2–C6-alkenyl, optionally substituted with one or more substituents selected from the group consisting of halogen, aryl, substituted aryl, heterocyclic, substituted heterocyclic, O—R7 and NR7R8, where R7 and R8 are as defined in claim 1; and
(3) C2–C6-alkynyl, optionally substituted with one or more substitutents selected from the group consisting of halogen, aryl, substituted aryl, heterocyclic, substituted heterocyclic, O—R7 and NR7R8, where R7 and R8 are as defined in claim 1.

3. A compound according to claim 2, wherein in R4, when M is absent, Y is hydrogen or a hydroxy protecting group.

4. A compound according to claim 1, wherein in R4, when M is absent, Y is:
(1) C1–C6-alkyl, optionally substituted with one or more substituents selected from the group consisting of halogen, aryl, substituted aryl, heterocyclic, substituted heterocyclic and O—R7, where R7 is as defined in claim 1,
(2) C2–C6-alkenyl, optionally substituted with one or more substituents selected from the group consisting of halogen, aryl, substituted aryl, heterocyclic, substituted heterocyclic and O—R7 where R7 is as defined in claim 1,
(3) C2–C6-alkynyl, optionally substituted with one or more substituents selected from the group consisting of halogen, aryl, substituted aryl, heterocyclic, substituted heterocyclic and O—R7 where R7 is as defined in claim 1,
(4) aryl,
(5) substituted aryl,
(6) heterocyclic, or
(7) substituted heterocyclic.

5. A compound according to claim 1 wherein R1 and R2 taken together=O, R3=H, R4=C2–C6-alkenyl, optionally substituted with one or more substituents substituted heterocyclic, where A and $R^P$ are as defined in claim 1.

6. A compound according to claim 1 wherein R1 and R2 taken together=O, R3=H, R4=C2–C6-alkynyl, optionally substituted with one or more substituents selected from the group consisting of aryl, substituted aryl, heterocyclic and substituted heterocyclic, where A and $R^P$ are as defined in claim 1.

7. A compound according to claim 1 wherein R1 and R2 taken together=O, R3=C2–C6-alkenyl, optionally substituted with one or more substituents selected from the group consisting of aryl, substituted aryl, heterocyclic and substituted heterocyclic, and R4=H, where A and $R^P$ are as defined in claim 1.

8. A compound according to claim 1 wherein R1 and R2 taken together=O, R3=C2–C6-alkynyl, optionally substituted with one or more substituents selected from the group consisting of aryl, substituted aryl, heterocyclic and substituted heterocyclic, and R4=H, where A and $R^P$ are as defined in claim 1.

9. A compound according to claim 1 which is selected from the group consisting of:

Compound of Formula I: A=—CHO, R1 and R2 taken together=O, R3=H, R4=—CH$_2$CHCH$_2$ and $R^P$=H;

Compound of Formula I: A=—CHO, R1 and R2 taken together=O, R3=—CH$_2$CHCH$_2$, R4=H and $R^P$=H;

Compound of Formula I: A=—CHO, R1 and R2 taken together=O, R3=H, R4=—CHCHCH$_2$-(3-quinolyl) and $R^P$=H;

Compound of Formula I: A=—CHO, R1 and R2 taken together=O, R3=H, R4=—CH$_2$CHCH-(3-quinolyl), and $R^P$=H;

Compound of Formula I: A=—CHO, R1 and R2 taken together=O, R3=—CH$_2$CHCH-phenyl, R4=H and $R^P$=H;

Compound of Formula I: A=—CHO, R1 and R2 taken together=O, R3=—CHCHCH$_2$-(3-quinolyl), R4=H and $R^P$=H; and Compound of Formula I: A=—CHO, R1 and R2 taken together=O, R3=—CH$_2$CHCH-(3-quinolyl), R4=H and $R^P$=H.

10. A pharmaceutical composition for treating bacterial infections comprising a therapeutically effective amount of a compound of claim 1 or a pharmaceutically acceptable salt, ester or prodrug thereof in combination with a pharmaceutically acceptable carrier.

11. A method for treating bacterial infections comprising administering to a mammal in need of such treatment a pharmaceutical composition containing a therapeutically-effective amount of a compound of claim 1 or a pharmaceutically acceptable salt, ester or prodrug thereof.

12. A process for the preparation of a compound represented by Formula I as defined in claim 1 comprising the steps:

(a) reacting a compound represented by the formula:

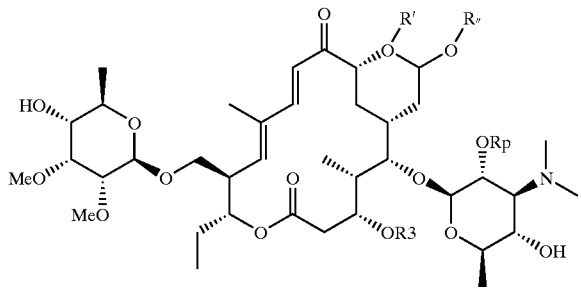

where $R^p$ is a hydroxy protecting group with a silylating agent, optionally with the addition of 4-N,N-dimethylaminopyridine or imidazole, in an aprotic solvent between 0° C. to 100° C. to provide a compound represented by the formula:

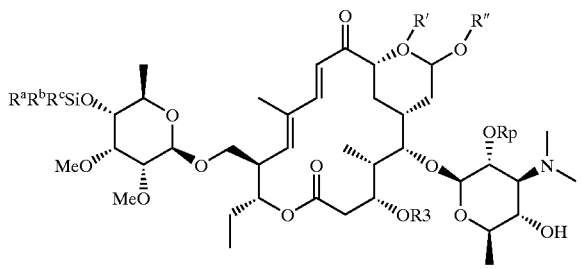

where R' and R" are each independently alkyl or when taken together=—CH$_2$—CH$_2$—, where $R^a$, $R^b$, and $R^c$ are each independently alkyl or aryl, and where $R^p$ is an ester or a silyl ether;

(b) reacting the compound from step(a) with an alkylating agent in the presence of a base in an aprotic solvent between −20° C. to 60° C. to provide a protected intermediate represented by the formula:

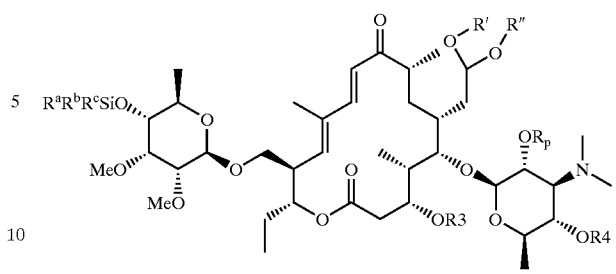

where R', R", $R^a$, $R^b$, $R^c$ and $R^p$ are as previously defined, where R4 is as defined in claim 1;

(c) reacting the protected intermediate from step (b) with an aqueous acid and tetrabutylammonium fluoride or hydrofluoric acid to provide a compound represented by Formula I of claim 1, where A=—CHO, R1 and R2 taken together=O, R3=H, R4 is as defined in claim 1 and $R^p$ is a hydroxy protecting group; and (d) reacting the compound from step (c) with methanol at a temperature between room temperature to reflux temperature to provide a compound represented by Formula I of claim 1 where A=—CHO, R1 and R2 taken together=O, R3 is hydrogen, R4 is as defined in claim 1 and $R^p$ is hydrogen.

13. A process for the preparation of a compound represented by Formula I as defined in claim 1 comprising the steps:

(a) reacting a compound represented by the formula:

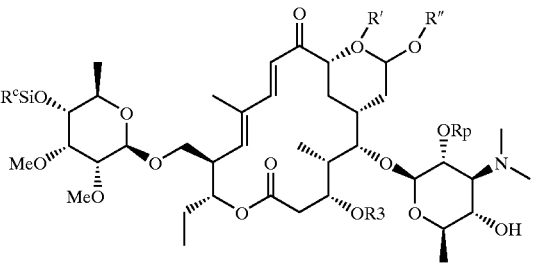

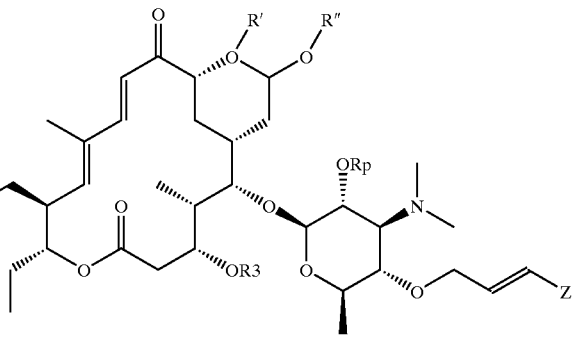

where R' and R" are each independently alkyl or when taken together=—CH$_2$—CH$_2$—, where $R^a$, $R^b$ and $R^c$ are each independently alkyl or aryl, and where $R^p$ is an ester or a silyl ether
with a tert-butyl allyl carbonate or an aryl tert-butyl allyl carbonate in the presence of a palladium catalyst to provide a compound represented by the formula:

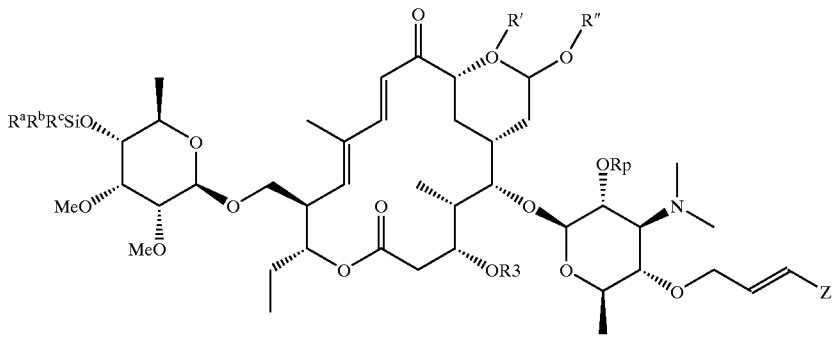

where R', R", $R^a$, $R^b$, $R^c$ and $R^p$ are as previously defined and where Z is hydrogen or aryl;

(b) reacting the compound from step (a) with an aqueous acid and tetrabutylammonium fluoride or hydrofluoric acid to provide a compound represented by Formula I in claim 1, where A=—CHO, R1 and R2 taken together=O, R3 is hydrogen, R4 is —CH$_2$CHCH—Z and $R^p$ is a hydroxy protecting group; and (c) reacting the compound from step (b) with methanol to provide a compound represented by Formula I of claim 1 where A=—CHO, R1 and R2 taken together=O, R3=H, R4 is —CH$_2$CHCH—Z and $R^p$=hydrogen.

14. A process for the preparation of a compound represented by Formula I as defined in claim 1 comprising the steps:

(a) reacting a compound represented by the formula:

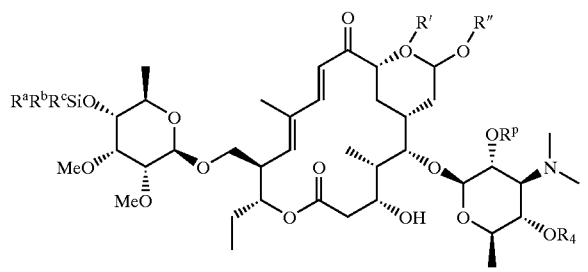

where R' and R" are each independently alkyl or when taken together are —CH$_2$—CH$_2$—, where $R^a$, $R^b$, $R^c$ are each independently alkyl or aryl, where R4 is as defined in claim 1 and where $R^p$ is an ester or a silyl ether with a tert-butyl allyl carbonate or an aryl tert-butyl allyl carbonate in the presence of a palladium catalyst to provide a compound represented by the formula:

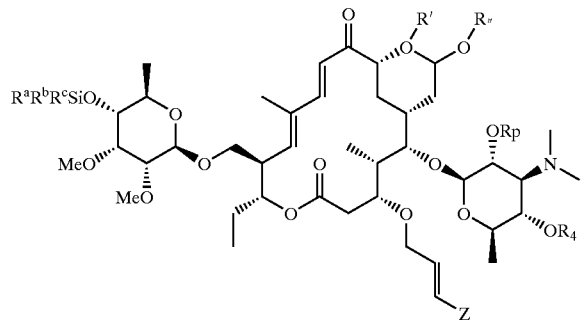

where R', R", $R^a$, $R^b$, $R^c$ and $R^p$ are as previously defined, Z is hydrogen or aryl, and R4 is as defined in claim 1;

(b) reacting the compound from step (a) with an aqueous acid and tetrabutylammoniun fluoride or hydrofluoric acid to provide a compound represented by Formula I in claim 1, where A=—CHO, R1 and R2 taken together=O, R3=—CH$_2$CHCH—Z, R4 is as defined in claim 1 and $R^p$ is a hydroxy protecting group; and (c) reacting the compound from step (b) with methanol at a temperature between room temperature to reflux temperature to provide a compound represented by Formula I in claim 1, where A=—CHO, R1 and R2 taken together=O, R3=—CH$_2$CHCH—Z, R4 is as defined in claim 1 and $R^p$=H.

* * * * *